(12) United States Patent
Foster

(10) Patent No.: US 10,398,793 B2
(45) Date of Patent: Sep. 3, 2019

(54) HAND SANITIZING ASSEMBLY

(71) Applicant: Alva Foster, West Palm Beach, FL (US)

(72) Inventor: Alva Foster, West Palm Beach, FL (US)

( * ) Notice: Subject to any disclaimer, the term of this patent is extended or adjusted under 35 U.S.C. 154(b) by 121 days.

(21) Appl. No.: 15/602,168

(22) Filed: May 23, 2017

(65) Prior Publication Data

US 2018/0339072 A1    Nov. 29, 2018

(51) Int. Cl.
| A61L 2/00  | (2006.01) |
| A61L 2/18  | (2006.01) |
| A47K 10/48 | (2006.01) |
| B05B 13/02 | (2006.01) |

(52) U.S. Cl.
CPC ............ *A61L 2/0088* (2013.01); *A47K 10/48* (2013.01); *B05B 13/0278* (2013.01); *A61L 2202/14* (2013.01); *A61L 2202/15* (2013.01)

(58) Field of Classification Search
CPC .................................. A61L 2/18; A47K 10/48
See application file for complete search history.

(56) References Cited

U.S. PATENT DOCUMENTS

| 2,814,081 | A   |   | 11/1957 | Stevenson |              |
|-----------|-----|---|---------|-----------|--------------|
| 3,918,117 | A   | * | 11/1975 | Plante    | A47K 7/04    |
|           |     |   |         |           | 15/88.3      |
| 3,918,987 | A   | * | 11/1975 | Kopfer    | A61H 35/00   |
|           |     |   |         |           | 134/113      |
| 4,999,929 | A   |   | 3/1991  | Dutton    |              |
| 5,074,322 | A   |   | 12/1991 | Jaw       |              |
| 5,265,628 | A   | * | 11/1993 | Sage      | A61B 90/80   |
|           |     |   |         |           | 134/103.3    |
| D592,807  | S   |   | 5/2009  | Todd et al. |            |
| 8,607,472 | B2  |   | 12/2013 | Ishi et al. |            |
| 2004/0083547 | A1 | * | 5/2004 | Mercier   | A47K 5/1217  |
|           |     |   |         |           | 4/623        |
| 2008/0099049 | A1 | * | 5/2008 | Barnhill  | A47K 7/04    |
|           |     |   |         |           | 134/18       |
| 2011/0016928 | A1 | * | 1/2011 | Beihoff   | D06F 58/203  |
|           |     |   |         |           | 68/19        |
| 2011/0171083 | A1 |   | 7/2011  | Swistak   |              |
| 2015/0037020 | A1 |   | 2/2015  | Troner    |              |
| 2015/0048160 | A1 |   | 2/2015  | Graydon   |              |

FOREIGN PATENT DOCUMENTS

WO    WO2012076521    6/2012

* cited by examiner

*Primary Examiner* — Kevin Joyner

(57) ABSTRACT

A hand sanitizing assembly for sanitizing and drying hands includes a tunnel unit that is positioned on a support surface. Hands are selectively placed in the tunnel unit. A sanitizing unit is positioned within the tunnel unit and the sanitizing unit contains a fluid sanitizer. The sanitizing unit selectively dispenses the fluid sanitizer to sanitize the hands when the hands are positioned in the tunnel unit. A blower unit is positioned within the tunnel unit to selectively urge air through the tunnel unit. In this way the hands are dried when the hands are sanitized.

15 Claims, 5 Drawing Sheets

US 10,398,793 B2

HAND SANITIZING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to sanitizing devices and more particularly pertains to a new sanitizing device for sanitizing and drying hands.

BRIEF SUMMARY OF THE INVENTION

An embodiment of the disclosure meets the needs presented above by generally comprising a tunnel unit that is positioned on a support surface. Hands are selectively placed in the tunnel unit. A sanitizing unit is positioned within the tunnel unit and the sanitizing unit contains a fluid sanitizer. The sanitizing unit selectively dispenses the fluid sanitizer to sanitize the hands when the hands are positioned in the tunnel unit. A blower unit is positioned within the tunnel unit to selectively urge air through the tunnel unit. In this way the hands are dried when the hands are sanitized.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
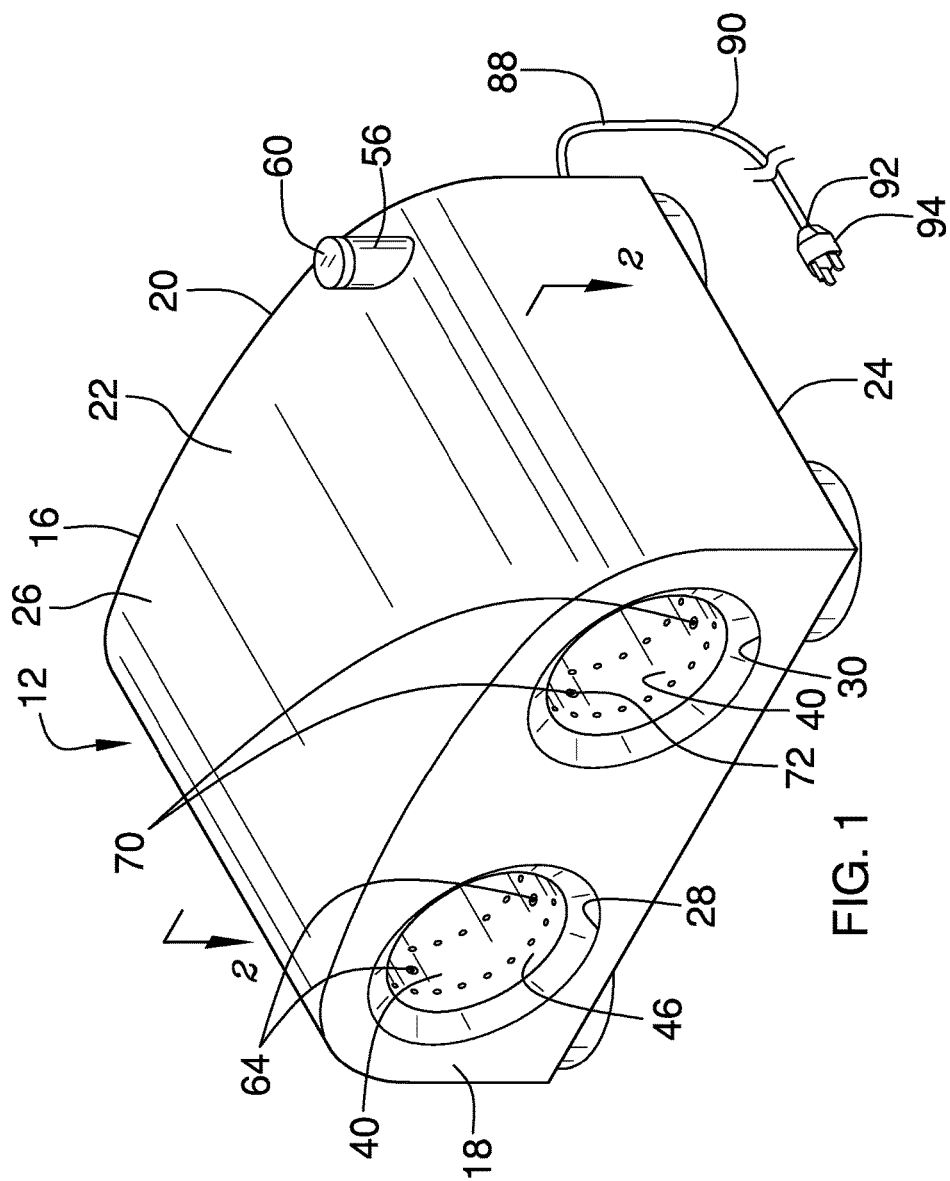
FIG. 1 is a top perspective view of a hand sanitizing assembly according to an embodiment of the disclosure.
Figure 2:
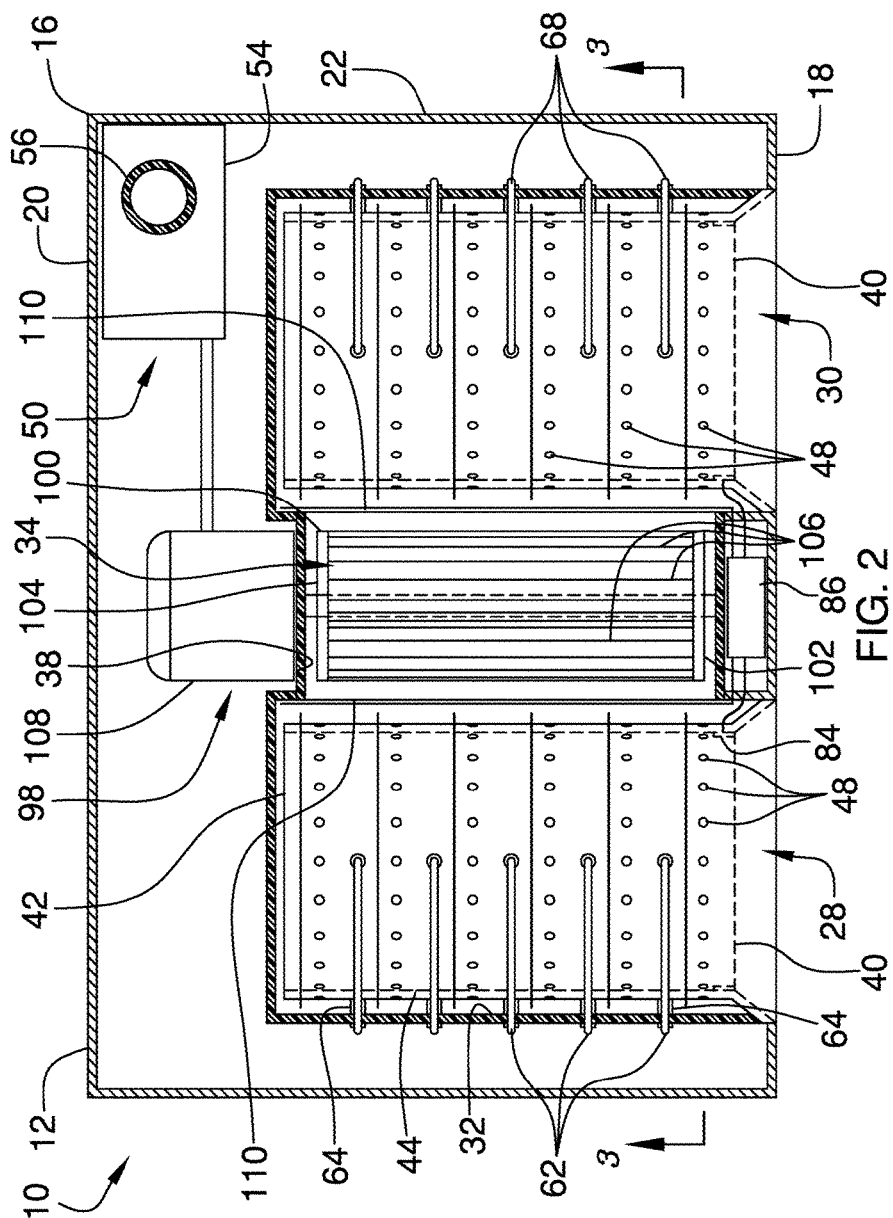
FIG. 2 is a cross sectional view taken along line 2-2 of FIG. 1 of an embodiment of the disclosure.
Figure 3:
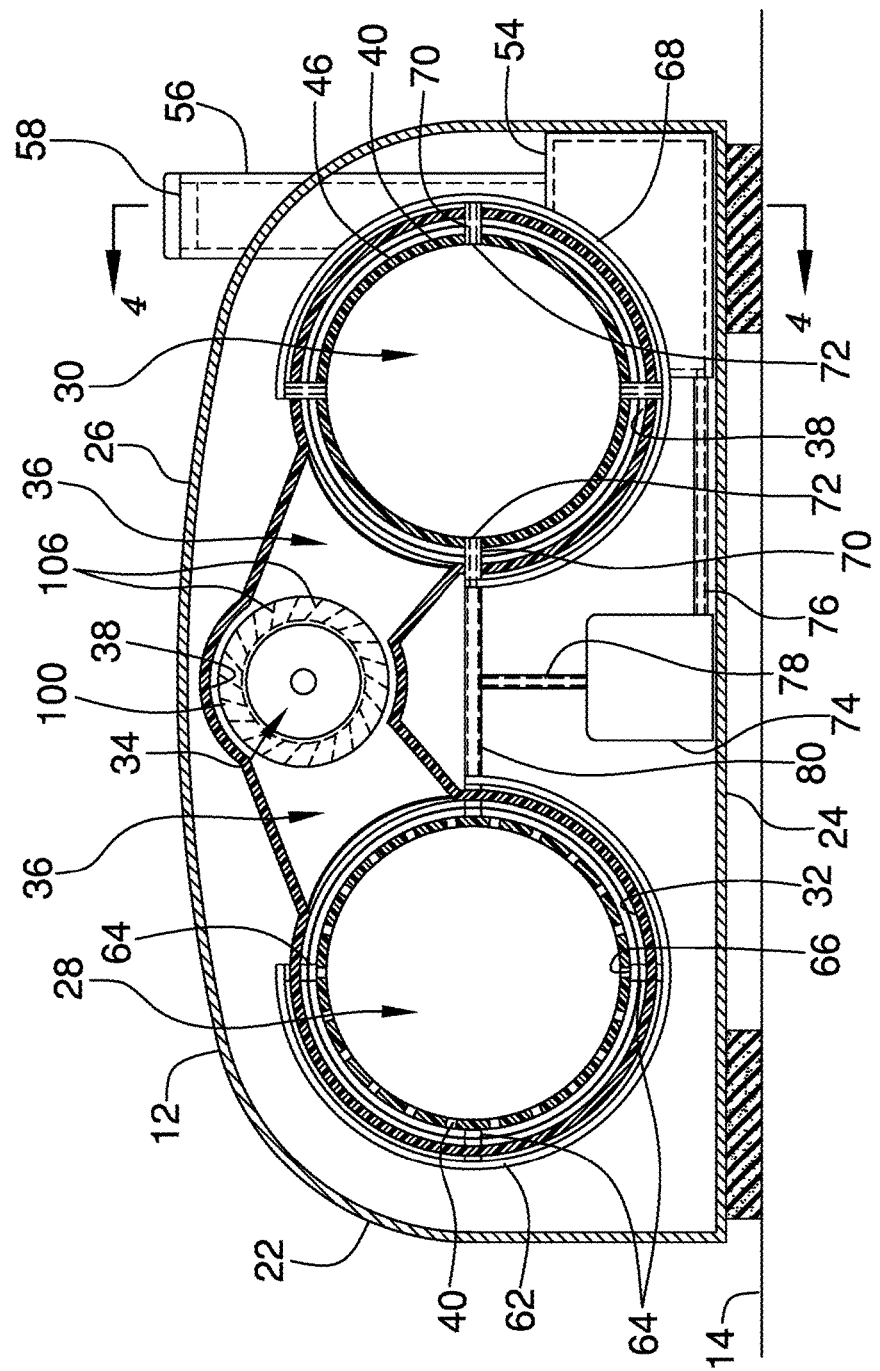
FIG. 3 is a cross sectional view taken along line 3-3 of FIG. 2 of an embodiment of the disclosure.
Figure 4:
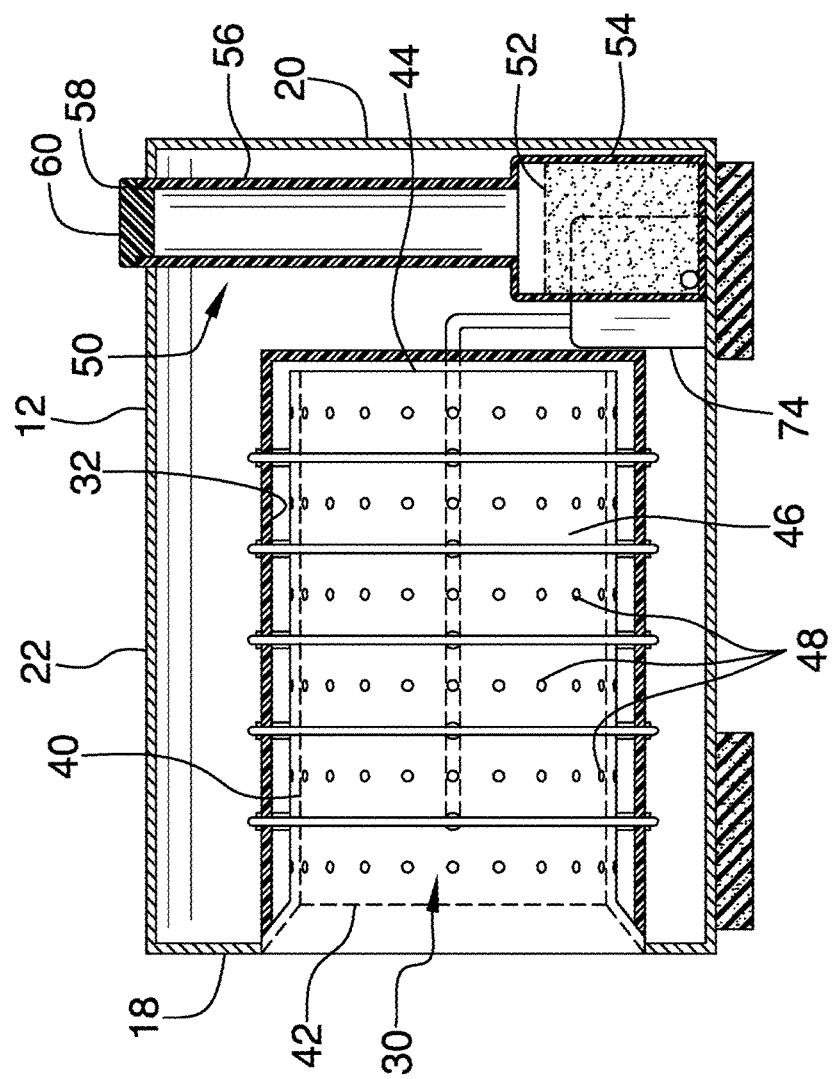
FIG. 4 is a cross sectional view taken along line 4-4 of FIG. 3 of an embodiment of the disclosure.
Figure 5:
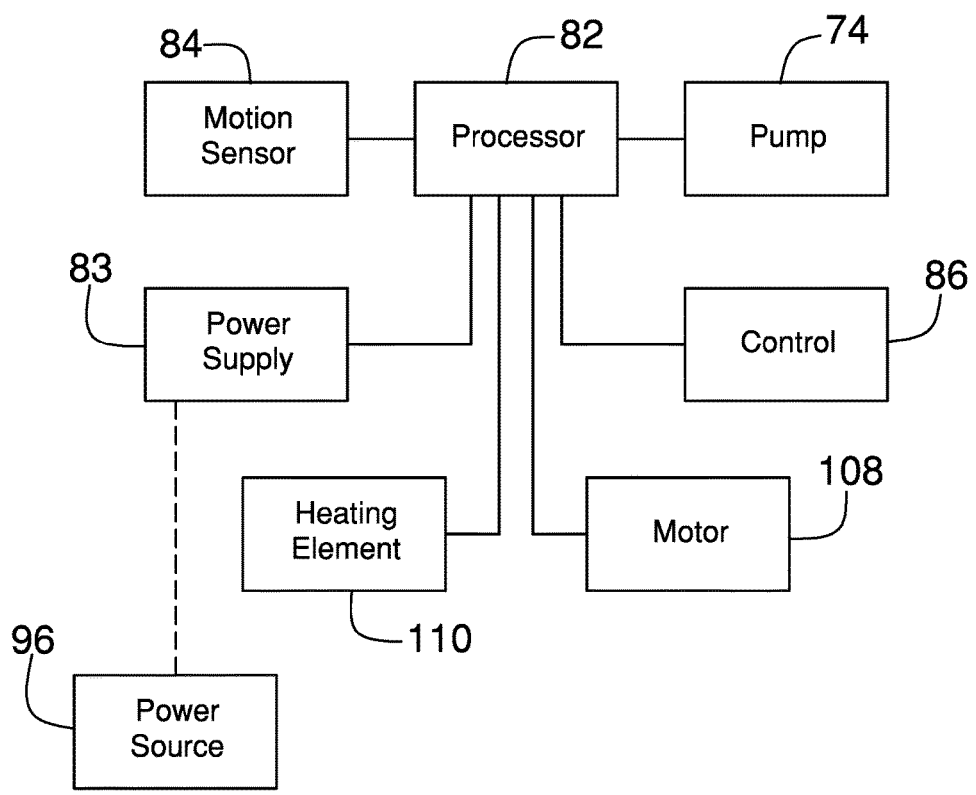
FIG. 5 is a schematic view of an embodiment of the disclosure.

With reference now to the drawings, and in particular to FIGS. 1 through 5 thereof, a new sanitizing device embodying the principles and concepts of an embodiment of the disclosure and generally designated by the reference numeral 10 will be described.

As best illustrated in FIGS. 1 through 5, the hand sanitizing assembly 10 generally comprises a tunnel unit 12 that is positioned on a support surface 14. The support surface 14 may be a table top, a wall or any other support surface 14. Additionally, the tunnel unit 12 may be positioned in a public area such as a restaurant, a public bathroom or any other area known to harbor bacteria from many people. The tunnel unit 12 comprises a housing 16 that has a front wall 18, a back wall 20 and an outer wall 22 extending therebetween. The outer wall 22 has a bottom side 24 and a top side 26, and the top side 26 is concavely arcuate with respect to the bottom side 24 such that the housing 16 has a quonset shape.

The housing 16 has a first well 28 extending through the front 18 and back 20 walls. The housing 16 has a second well 30 extending through the front 18 and back 20 walls. Each of the first 28 and second 30 wells has a bounding surface 32. Moreover, the housing 16 has a chamber 34 extending substantially between the front 18 and back 20 walls. The housing 16 has a pair of ducts 36 and each of the ducts 36 intersects the chamber 34 and an associated one of the first 28 and second 30 wells. In this way the chamber 34 is in fluid communication with each of the first 28 and second 30 wells. The chamber 34 has a bounding surface 38 and the bounding surface 38 corresponding to the chamber 34 is continuous such that the chamber 34 has a cylindrical shape.

A pair of sleeves 40 is provided and each of the sleeves 40 has a first end 42, a second end 44 and an exterior wall 46 extending therebetween. Each of the sleeves 40 is positioned within an associated one of the first 28 and second 30 wells. The first end 42 and the second end 44 corresponding to each of the sleeves 40 are aligned with an associated one of the front wall 18 and the back wall 20. Moreover, the exterior wall 46 corresponding to each of the sleeves 40 is spaced from the bounding surface 32 of the associated first 28 and second 30 wells. The exterior wall 46 corresponding to each of the sleeves 40 has a plurality of openings 48 extending into an interior of the corresponding sleeve 40.

The openings 48 are spaced apart from each other and are distributed in a plurality of rows on the corresponding sleeve 40.

A sanitizing unit 50 is positioned within the tunnel unit 12 and the sanitizing unit 50 contains a fluid sanitizer 52. The sanitizing unit 50 selectively dispenses the fluid sanitizer 52 onto hands. The fluid sanitizer 52 may be an anti-bacterial hand sanitizer of any conventional design to kill bacteria on the hands. Thus, the hands are sanitized when the hands are positioned in the tunnel unit 12.

The sanitizing unit 50 comprises a reservoir 54 that is positioned within the housing 16 and the reservoir 54 contains the fluid sanitizer 52. A spout 56 is coupled to and extends upwardly from the reservoir 54 such that the spout 56 is in fluid communication with the reservoir 54. The spout 56 has a distal end 58 with respect to the reservoir 54 and the distal end 58 is open. The spout 56 extends through the top side 26 of the housing 16 and the distal end 58 is exposed for filling the reservoir 54. A cap 60 is removably positioned on the distal end 58 to close the distal end 58.

A set of first tubes 62 is provided and each of the first tubes 62 extends substantially around the sleeve 40 corresponding to the first well 28. The first tubes 62 are spaced apart from each other and are distributed between the first 42 and second 44 ends of the corresponding sleeve 40. Each of the first tubes 62 has a plurality of first nozzles 64 that are fluidly coupled thereto. Moreover, each of the first nozzles 64 extends through the corresponding sleeve 40 and into the first well 28. Each of the first nozzles 64 has a distal end 66 with respect to the corresponding sleeve 40 and the distal end 66 corresponding to each of the first nozzles 64 is open.

A set of second tubes 68 is provided and each of the second tubes 68 extends substantially around the sleeve 40 corresponding to the second well 30. The second tubes 68 are spaced apart from each other and are distributed between the first 42 and second ends 44 of the corresponding sleeve 40. Each of the second tubes 68 has a plurality of second nozzles 70 that are fluidly coupled thereto. Moreover, each of the second nozzles 70 extends through the corresponding sleeve 40 and into the second well 30. Each of the second nozzles 70 has a distal end 72 with respect to the corresponding sleeve 40 and the distal end 72 corresponding to each of the second nozzles 70 is open.

A pump 74 is positioned within the housing 16 and the pump 74 has an input 76 and an output 78. The input 76 is in fluid communication with the reservoir 54 such that the pump 74 selectively urges the fluid sanitizer 52 outwardly from the output 78. The pump 74 may be an electric fluid pump or the like. A conduit 80 is fluidly coupled between the output 78 and each of the first 62 and second 98 tubes. In this way the conduit 80 directs the fluid sanitizer 52 outwardly through each of the first 64 and second 70 nozzles to be dispensed onto the hands.

A processor 82 is positioned within the housing 16 and the processor 82 is electrically coupled to the pump 74. The processor 82 selectively generates an on sequence and the pump 74 is turned on when the processor 82 generates the on sequence. The processor 82 may be an electronic processor or the like. Additionally, the processor 82 may include an electronic timer and the electronic timer may cease the on sequence after a pre-determined duration of time.

A motion sensor 84 is coupled to the housing 16 and the motion sensor 84 is electrically coupled to the processor 82. The motion sensor 84 is positioned in a selected one of the sleeves 40 to sense motion. In this way the motion sensor 84 detects when the hands are positioned in the selected sleeve. The processor 82 generates the on sequence when the motion sensor 84 senses motion. Additionally, a pair of the motion sensors 84 may be provided and each of the motion sensors 84 may comprise an electronic motion sensor or the like.

A control 86 is coupled to the housing 16 and the control 86 is selectively manipulated. The control 86 is electrically coupled to the processor 82 such that the control 86 controls operational parameters of the processor 82. The control 86 may include a plurality of buttons, a touch pad or any other conventional electronic means of controlling the processor 82. A power supply 88 is positioned in the housing 16 and the power supply 88 is electrically coupled to the processor 82. The power supply 88 comprises a power cord 90 extending outwardly from the housing 16. The power cord 90 has a distal end 92 with respect to the housing 16 and a plug 94 is electrically coupled to the distal end 92 of the power cord 90. The plug 94 is electrically coupled to a power source 96 such as a female electrical outlet or the like.

A blower unit 98 is positioned within the tunnel unit 12 and the blower unit 98 selectively urges air through the tunnel unit 12. In this way the hands are dried when the hands are sanitized. The blower unit 98 comprises a fan 100 that has a primary end 102 and a secondary end 104. The fan 100 is elongated between the primary end 102 and the secondary end 104 and the fan 100 includes a plurality of blades 106. Each of the blades 106 is spaced apart from each other and extends between the primary 102 and secondary 104 ends.

The fan 100 is rotatably positioned within the chamber 34 such that the fan 100 urges air through each of the ducts 36, into each of the first 28 and second 30 wells and outwardly through the openings 48 in each of the sleeves 40. In this way the fan 100 dries the hands when the hands are positioned in the tunnel unit 12. A motor 108 is coupled to the fan 100 such that the motor 108 rotates the fan 100 when the motor 108 is turned on. The motor 108 is electrically coupled to the processor 82 such that the motor 108 is turned on when the processor 82 generates the on sequence. Moreover, the motor 108 may comprise an electric motor or the like.

A plurality of heating elements 110 is provided and each of the heating elements 110 is positioned around the fan 100. Each of the heating elements 110 is electrically coupled to the processor 82 and the processor 82 turns each of the heating elements 110 on when the processor 82 generates the on sequence. Thus, the heating elements 110 heat the air urged by the fan 100 to enhance drying the hands. Each of the heating elements 110 may comprise an electrical heating element or the like.

In use, the hands are positioned in each of the sleeves 40 and the motion sensor 84 senses the motion of the hands. The processor 82 generates the on sequence when the motion sensor 84 senses the motion to turn on the pump 74 and the motor 108. The pump 74 urges the fluid sanitizer 52 outwardly through each of the sleeves 40 such that the fluid sanitizer 52 is sprayed on the hands. In this way the hands are sanitized when the hands are inserted into the sleeves 40. Additionally, the fan 100 is turned on when the processor 82 generates the on sequence to dry the hands. In this way the hands are cleaned and dried without having the hands touch a surface thereby enhancing cleanliness and inhibiting the transfer of bacteria between individuals.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A hand sanitizing assembly being configured to automatically sanitize and dry hands, said assembly comprising:
    a tunnel unit being configured to be positioned on a support surface, said tunnel unit being configured to have hands positioned therein, said tunnel unit comprising a housing having a front wall, a back wall and an outer wall extending therebetween, said outer wall having a bottom side and a top side, said top side being concavely arcuate with respect to the bottom side such that said housing has a quonset shape, said housing having a first well extending through said front and back walls, said housing having a second well extending through said front and back walls, each of said first and second wells having a bounding surface, said housing having a chamber extending substantially between said front and back walls, said housing having a pair of ducts, each of said ducts intersecting said chamber and an associated one of said wells such that said chamber is in fluid communication with each of said first and second wells, said chamber having a bounding surface, said bounding surface corresponding to said chamber being continuous such that said chamber has a cylindrical shape, said tunnel unit having a pair of sleeves, each of said sleeves having a plurality of openings;
    a sanitizing unit being positioned within said tunnel unit, said sanitizing unit containing a fluid sanitizer, said sanitizing unit selectively dispensing said fluid sanitizer wherein said sanitizing unit is configured to sanitize the hands when the hands are positioned in said tunnel unit; and
    a blower unit being positioned within said tunnel unit wherein said blower unit is configured to selectively urge air through said tunnel unit thereby facilitating the hands to be dried when the hands are sanitized, said blower unit including a fan having a primary end and a secondary end, said fan being elongated between said primary end and said secondary end, said fan comprising a plurality of blades, each of said blades being spaced apart from each other and extending between said primary and secondary ends, said fan being rotatably positioned within said chamber such that said fan urges air through each of said ducts, into each of said first and second wells and outwardly through each of said openings in each of said sleeves wherein said fan is configured to dry the hands when the hands are positioned in said tunnel unit.

2. The assembly according to claim 1, further comprising a pair of sleeves, each of said sleeves having a first end, a second end and an exterior wall extending therebetween, each of said sleeves being positioned within an associated one of said first and second wells having said first end and said second end corresponding to each of said sleeves being aligned with an associated one of said front wall and said back wall and having said exterior wall being spaced from said bounding surface of said associated first and second well.

3. The assembly according to claim 2, wherein said exterior wall corresponding to each of said sleeves has a plurality of openings extending into an interior of said corresponding sleeve, said openings being spaced apart from each other and being distributed in a plurality of rows on said corresponding sleeve.

4. The assembly according to claim 1, wherein said sanitizing unit comprises a reservoir being positioned within said housing, said reservoir containing said fluid sanitizer.

5. The assembly according to claim 4, further comprising:
    a spout being coupled to and extending upwardly from said reservoir such that said spout is in fluid communication with said reservoir, said spout having a distal end with respect to said reservoir, said distal end being open, said spout extending through said top side of said housing having said distal end being exposed for filling said reservoir; and
    a cap being removably positioned on said distal end to close said distal end.

6. The assembly according to claim 4, further comprising a pump being positioned within said housing, said pump having an input and an output, said input being in fluid communication with said reservoir such that said pump selectively urges said fluid sanitizer outwardly from said output.

7. The assembly according to claim 6, further comprising:
    a first tube having a plurality of first nozzles;
    a second tube having a plurality of second nozzles; and
    a conduit being fluidly coupled between said output and each of said first and second tubes such that conduit directs said fluid sanitizer outwardly through each of said first and second nozzles wherein said fluid sanitizer is configured to be dispensed onto the hands.

8. The assembly according to claim 6, further comprising:
    a processor being positioned within said housing, said processor being electrically coupled to said pump, said processor selectively generating an on sequence, said pump being turned on when said processor generates said on sequence;
    a pair of sleeves; and
    a motion sensor being coupled to said housing, said motion sensor being electrically coupled to said processor, said motion sensor being positioned in a selected one of said sleeves wherein said motion sensor is configured to sense motion thereby facilitating said motion sensor to detect when the hands are positioned in said selected sleeve, said processor generating said on sequence when said motion sensor senses motion.

9. The assembly according to claim 8, further comprising:
    a control being coupled to said housing wherein said control is configured to be manipulated, said control being electrically coupled to said processor such that said control controls operational parameters of said processor; and
    a power supply being positioned in said housing, said power supply being electrically coupled to said processor, said power supply comprising a power cord extending outwardly from said housing, said power cord having a distal end with respect to said housing, said distal end of said power cord having a plug being electrically coupled thereto wherein said plug is configured to be electrically coupled to a power source.

10. The assembly according to claim 1, further comprising:
a pair of sleeves, each of said sleeves being positioned in an associated one of said first and second wells; and
a set of first tubes, each of said first tubes extending substantially around said sleeve corresponding to said first well, said first tubes being spaced apart from each other and being distributed between said first and second ends of said corresponding sleeve.

11. The assembly according to claim 10, wherein each of said first tubes has a plurality of first nozzles being fluidly coupled thereto, each of said first nozzles extending through said corresponding sleeve and into said first well, each of said first nozzles having a distal end with respect to said corresponding sleeve, said distal end corresponding to each of said first nozzles being open.

12. The assembly according to claim 1, further comprising:
a pair of sleeves, each of said sleeves being positioned in an associated one of said first and second wells; and
a set of second tubes, each of said second tubes extending substantially around said sleeve corresponding to said second well, said second tubes being spaced apart from each other and being distributed between said first and second ends of said corresponding sleeve.

13. The assembly according to claim 12, wherein each of said second tubes has a plurality of second nozzles being fluidly coupled thereto, each of said second nozzles extending through said corresponding sleeve and into said second well, each of said second nozzles having a distal end with respect to said corresponding sleeve, said distal end corresponding to each of said second nozzles being open.

14. The assembly according to claim 1, further comprising:
a processor selectively generating an on sequence; and
a motor being coupled to said fan such that said motor rotates said fan when said motor is turned on, said motor being electrically coupled to said processor such that said motor is turned on when said processor generates said on sequence.

15. A hand sanitizing assembly being configured to automatically sanitize and dry hands, said assembly comprising:
a tunnel unit being configured to be positioned on a support surface, said tunnel unit being configured to have hands positioned therein, said tunnel unit comprising:
a housing having a front wall, a back wall and an outer wall extending therebetween, said outer wall having a bottom side and a top side, said top side being concavely arcuate with respect to the bottom side such that said housing has a quonset shape, said housing having a first well extending through said front and back walls, said housing having a second well extending through said front and back walls, each of said first and second wells having a bounding surface, said housing having a chamber extending substantially between said front and back walls, said housing having a pair of ducts, each of said ducts intersecting said chamber and an associated one of said wells such that said chamber is in fluid communication with each of said first and second wells, said chamber having a bounding surface, said bounding surface corresponding to said chamber being continuous such that said chamber has a cylindrical shape, and
a pair of sleeves, each of said sleeves having a first end, a second end and an exterior wall extending therebetween, each of said sleeves being positioned within an associated one of said first and second wells having said first end and said second end corresponding to each of said sleeves being aligned with an associated one of said front wall and said back wall and having said exterior wall being spaced from said bounding surface of said associated first and second well, said exterior wall corresponding to each of said sleeves having a plurality of openings extending into an interior of said corresponding sleeve, said openings being spaced apart from each other and being distributed in a plurality of rows on said corresponding sleeve;
a sanitizing unit being positioned within said tunnel unit, said sanitizing unit containing a fluid sanitizer, said sanitizing unit selectively dispensing said fluid sanitizer wherein said sanitizing unit is configured to sanitize the hands when the hands are positioned in said tunnel unit, said sanitizing unit comprising:
a reservoir being positioned within said housing, said reservoir containing said fluid sanitizer,
a spout being coupled to and extending upwardly from said reservoir such that said spout is in fluid communication with said reservoir, said spout having a distal end with respect to said reservoir, said distal end being open, said spout extending through said top side of said housing having said distal end being exposed for filling said reservoir,
a cap being removably positioned on said distal end to close said distal end,
a set of first tubes, each of said first tubes extending substantially around said sleeve corresponding to said first well, said first tubes being spaced apart from each other and being distributed between said first and second ends of said corresponding sleeve, each of said first tubes having a plurality of first nozzles being fluidly coupled thereto, each of said first nozzles extending through said corresponding sleeve and into said first well, each of said first nozzles having a distal end with respect to said corresponding sleeve, said distal end corresponding to each of said first nozzles being open,
a set of second tubes, each of said second tubes extending substantially around said sleeve corresponding to said second well, said second tubes being spaced apart from each other and being distributed between said first and second ends of said corresponding sleeve, each of said second tubes having a plurality of second nozzles being fluidly coupled thereto, each of said second nozzles extending through said corresponding sleeve and into said second well, each of said second nozzles having a distal end with respect to said corresponding sleeve, said distal end corresponding to each of said second nozzles being open,
a pump being positioned within said housing, said pump having an input and an output, said input being in fluid communication with said reservoir such that said pump selectively urges said fluid sanitizer outwardly from said output,
a conduit being fluidly coupled between said output and each of said first and second tubes such that conduit directs said fluid sanitizer outwardly through each of said first and second nozzles wherein said fluid sanitizer is configured to be dispensed onto the hands, a processor being positioned within said housing, said processor being electrically coupled to said pump, said processor selectively generating an on sequence, said pump being turned on when said processor generates said on sequence, a motion sensor being coupled to said housing, said motion sensor being electrically coupled to said processor, said motion sensor being positioned in a selected one of said sleeves wherein said motion sensor is configured to sense motion thereby facilitating said motion sensor to detect when the hands are positioned in said selected sleeve, said processor generating said on sequence when said motion sensor senses motion, a control being coupled to said housing wherein said control is configured to be manipulated, said control being electrically coupled to said processor such that said control controls operational parameters of said processor, and a power supply being positioned in said housing, said power supply being electrically coupled to said processor, said power supply comprising a power cord extending outwardly from said housing, said power cord having a distal end with respect to said housing, said distal end of said power cord having a plug being electrically coupled thereto wherein said plug is configured to be electrically coupled to a power source; and a blower unit being positioned within said tunnel unit wherein said blower unit is configured to selectively urge air through said tunnel unit thereby facilitating the hands to be dried when the hands are sanitized, said blower unit comprising:

a fan having a primary end and a secondary end, said fan being elongated between said primary end and said secondary end, said fan comprising a plurality of blades, each of said blades being spaced apart from each other and extending between said primary and secondary ends, said fan being rotatably positioned within said chamber such that said fan urges air through each of said ducts, into each of said first and second wells and outwardly through said openings in each of said sleeves wherein said fan is configured to dry the hands when the hands are positioned in said tunnel unit, and a motor being coupled to said fan such that said motor rotates said fan when said motor is turned on, said motor being electrically coupled to said processor such that said motor is turned on when said processor generates said on sequence.

* * * * *